US010610538B2

(12) United States Patent
Balzarini et al.

(10) Patent No.: US 10,610,538 B2
(45) Date of Patent: Apr. 7, 2020

(54) PRADIMICIN DERIVATIVES FOR THE TREATMENT OF DISEASES CAUSED BY KINETOPLASTIDS

(71) Applicants: KATHOLIEKE UNIVERSITEIT LEUVEN, Leuven (BE); CONSEJO SUPERIOR DE INVESTIGACIONES CIENTÍFICASCSIC, Seville (ES)

(72) Inventors: Jan Balzarini, Heverlee (BE); Dolores González Pacanowska, Armilla-Granada (ES); Luis Miguel Ruiz Pérez, Armilla-Granada (ES); Victor Castillo Acosta, Armilla-Granada (ES); Yasuhiro Igarashi, Toyama (JP)

(73) Assignees: Katholieke Universiteit Leuven, Leuven (BE); Consejo Superior de Investigaciones Científicas - CSIC, Seville (ES)

( * ) Notice: Subject to any disclaimer, the term of this patent is extended or adjusted under 35 U.S.C. 154(b) by 332 days.

(21) Appl. No.: 15/027,465
(22) PCT Filed: Oct. 10, 2013
(86) PCT No.: PCT/BE2013/000055
§ 371 (c)(1),
(2) Date: Apr. 6, 2016
(87) PCT Pub. No.: WO2015/051422
PCT Pub. Date: Apr. 16, 2015

(65) Prior Publication Data
US 2016/0243140 A1 Aug. 25, 2016

(51) Int. Cl.
A61K 31/704 (2006.01)
(52) U.S. Cl.
CPC ........... A61K 31/704 (2013.01); Y02A 50/409 (2018.01); Y02A 50/414 (2018.01); Y02A 50/415 (2018.01)
(58) Field of Classification Search
None
See application file for complete search history.

(56) References Cited

U.S. PATENT DOCUMENTS

2009/0042793 A1* 2/2009 Balzarini ............. A61K 31/165
514/6.9

OTHER PUBLICATIONS

Castillo-Acosta, V. M. et al., Trends in Parasitology, "Surface Glycans: A Therapeutic Opportunity for Kinetoplastid Diseases", Oct. 2017, vol. 33, No. 10, pp. 775-787 (Year: 2017).*
Fung-Tomc, J. C. et al., Expert Opinion on Investigational Drugs, "Recent developments in pradimicin-benanomicin and triazole antibiotics", 1997, vol. 6, No. 2, pp. 129-145 (Year: 1997).*

(Continued)

*Primary Examiner* — Shaojia A Jiang
*Assistant Examiner* — Bahar Craigo
(74) *Attorney, Agent, or Firm* — Amster, Rothstein & Ebenstein LLP

(57) ABSTRACT

The present invention relates to a class of novel pradimicins and analogues and derivatives thereof, including the compounds of formula A, I and III, and/or a pharmaceutical acceptable addition salt thereof and/or a stereoisomer thereof and/or a solvate thereof and their use to treat or prevent kinetoplastid infections and their use to manufacture a medicine to treat or prevent kinetoplastid infections, particularly infections with *trypanosoma* and *leishmania*, such as *Trypanosoma brucei*, *Trypanosoma cruzi* and *Leishmania donovani*. wherein $R^a$, $R^1$, $R^2$, $R^3$, $R^4$, $R^5$, $R^6$, $R^7$, $R^8$ and $R^9$ are as defined in the claim 1 or as described in detail in the description of the invention. The present invention also relates to pharmaceutical compositions of said compounds and the use of said pharmaceutical compositions to treat or prevent kinetoplastid infections. The present invention further relates active ingredients, more specifically as medicaments for the treatment of kinetoplastid infections and pathologic conditions such as, but not limited to Trypanosomiasis, such as African trypanosomiasis, sleeping sickness, Chagas disease and leishmaniasis.

(Continued)

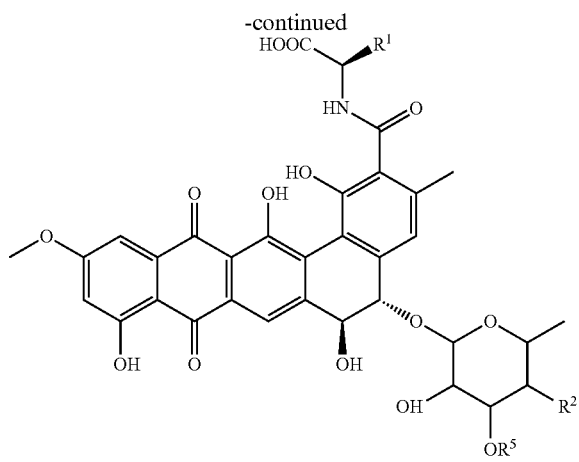

-continued

8 Claims, 2 Drawing Sheets

(56) References Cited

OTHER PUBLICATIONS

PCT International Search Report and Written Opinion dated Jul. 15, 2014 for PCT International Patent Application No. PCT/BE2013/000055, 9 pages.
Pearson, T W et al., entitled "The Major Cell Surface Glycoprotein Procyclin is a Receptor for Induction of a Novel Form of Cell Death in African trypanosomes in Vitro," Molecular and Biochemical Parasitology, vol. 111, 2000, pp. 333-349.
Balzarini, J et al., entitled "Pradimicin A, a Carbohydrate-Binding Nonpeptidic Lead Compound for Treatment of Infections With Viruses with Highly Glycosylated Envelopes Such as Human Deficiency Virus," Journal of Virology, vol. 81, 2007, pp. 362-373.
Castillo-Acosta, V M et al., entitled "Carbohydrate-binding agents act as potent trypanocidals that elicit modifications in VSG glycosylation and reduced virulence in Trypanosoma brucei," Molecular Microbiology, vol. 90, 2013, pp. 665-679, and Supporting Information.

\* cited by examiner

PRADIMICIN DERIVATIVES FOR THE TREATMENT OF DISEASES CAUSED BY KINETOPLASTIDS

CROSS-REFERENCE TO RELATED APPLICATION

This application is a U.S. national stage entry under 35 U.S.C. § 371 of PCT International Patent Application No. PCT/BE2013/000055, filed Oct. 10, 2013, the contents of which are incorporated herein by reference in their entirety.

FIELD OF THE INVENTION

The present invention relates to a class of novel pradimicins and analogues and derivatives thereof and their use to treat or prevent kinetoplastid infections and their use to manufacture a medicine to treat or prevent kinetoplastid infections, particularly infections with *Trypanosoma* and *Leishmania*, such as *Trypanosoma brucei*, *Trypanosoma cruzi* and *Leishmania donovani*.

STATE OF THE ART

Carbohydrate-binding agents (CBAs) have been proposed as an original therapeutic concept against various viral infections, such as human immunodeficiency virus (HIV) and human hepatitis C virus. CBAs are compounds that are capable of selectively targeting to surface glycans and can be of both peptidic and non-peptidic origin. Binding of CBAs to the glycans of the viral envelope directly blocks virus entry (Balzarini, 2007).

The protozoan parasite *Trypanosoma brucei* is the etiologic agent of African trypanosomiasis or sleeping sickness in human or nagana in domestic livestock. The chemotherapy of African trypanosomiasis relies on a few drugs which have adverse side-effects. Treatment depends on the stage of the disease. In the first stage of the disease the drugs available are of lower toxicity. For treatment of the second stage of the disease, a drug that can cross the blood-brain barrier is required. Second stage drugs are more toxic. The drugs used for the treatment of the first stage of the disease are pentamidine (well tolerated by patients) and suramin that has undesirable effects in the urinary tract and produces allergic reactions. For second stage treatment melarsoprol (an arsenical) is used. Melarsoprol has several side effects such as reactive encephalopathy (encephalopathic syndrome) which can be fatal. Resistance to melarsoprol has been repeatedly described. Eflornithine is only effective against second stage *T. b. gambiense*. The regimen is strict and difficult to apply. More recently a combination of nifurtimox and eflornithine is also being used for *T. b. gambiense*. Thus, drug resistance and the limited number of alternatives of treatment clearly justify the need for new drugs that are safe, effective and affolrdable.

*Trypanosoma cruzi* is the etiological agent of American trypanosomiasis or Chagas disease affecting more than 10 million people in Central and South America, with high rates of morbidity and mortality. Two drugs, nifurtimox and benznidazole, are capable of curing at least 50% of recent infections. These products are active in the acute and short-term chronic phase yet drugs with activity in long-term chronic forms of the disease are needed.

Leishmaniasis comprises a series of pathologies caused by different species of the *Leishmania* genus. According to disease burden estimates, leishmaniasis ranks third in disease burden in disability-adjusted life years caused by neglected tropical diseases. *Leishmania donovani* is responsible for visceral leishmaniasis, one of the most severe forms of the disease. The existing chemotherapeutic treatments do not have the desirable efficiency. Currently used drugs are pentavalent antimonial (SbV) compounds, liposomal amphotericin B and miltefosine. Amphotericin B deoxycholate, various "azoles" (ketoconazole, itraconazole, and fluconazole), and pentamidine have been also used. Miltefosine has the problem of potential reproductive toxicities in females and antimonials have in occasion adverse side effects (nausea and vomiting, arthralgia, hepatitis, pancreatitis and cardiac dysrhythmias).

In the case of trypanosomes, CBAs may provide therapeutic potential by binding to surface glycoproteins and impairing normal cell function. The cell surface of bloodstream *Trypanosoma brucei* (the causative agent of sleeping sickness) is covered by a densely packed coat of glycosylphosphatidylinositol-anchored proteins particularly the variant surface glycoproteins (VSGs) that physically protect underlying proteins from effectors of the host immune system like the antibodies. In addition, VSGs play a main role in virulence through antigenic variation which is an immune evasion strategy that involves stochastic switches in the composition of a VSG coat, using a massive archive of silent VSG genes to change the identity of the single expressed VSG (Morrison et al., 2009). In previous studies, cessation of cell division and profound morphological changes have been described in procyclic forms but not in the clinically relevant bloodstream forms after incubation with lectins (peptidic CBAs) such as concanavalin A, wheat germ agglutinin (WGA) and *Ricinus communis* agglutinin (RCA) (Pearson et al., 2000). The prevalent concept was that either lack of binding or rapid internalization and elimination of glycoprotein-lectin complexes via endocytosis and lectin degradation in the lysosome would result in low cellular toxicity in the bloodstream forms.

In conclusion, there is still a huge need for specific and highly therapeutically and non-toxic medication for the prevention or treatment of diseases caused by kinetoplastids, such as *Trypanosoma* sp. and *Leishmania*. Current treatments still have serious side effects.

SUMMARY OF THE INVENTION

The present invention is based on the unexpected finding that carbohydrate binding agents (CBAs), more specifically a series of non-peptidic CBAs, including compounds of formula I, PRM-A, PRM-S and derivatives are useful for the prevention or treatment of parasitic diseases such as diseases caused by kinetoplastids, such as *Trypanosoma* sp. and *Leishmania*. None of the prior art available to date discloses or suggests the precise use of these non-peptidic CBAs, especially the compounds of the present invention, that recognize specifically alfa(1,2)-mannose, for the prevention or treatment of parasitic diseases such as diseases caused by kinetoplastids, such as *Trypanosoma* sp. and *Leishmania*.

In this invention it is shown that a series of non-peptidic CBAs are able to specifically interact with surface glycoproteins giving rise to toxic events in bloodstream forms of parasites such as *Trypanosoma brucei*. They also proved to be active against infective trypomastigote forms of *Trypanosoma cruzi*, and intracellular amastigotes of *Leishmania donovani*. Therefore, this invention provides for the use of these non-peptidic carbohydrate binding agents (CBAs), including compounds of formula I, PRM-A, PRM-S and derivatives for the prevention or treatment of diseases caused by kinetoplastids, such as *Trypanosoma* sp. and *Leishmania*.

The present invention concerns the use of a compound of formula A, I or III:

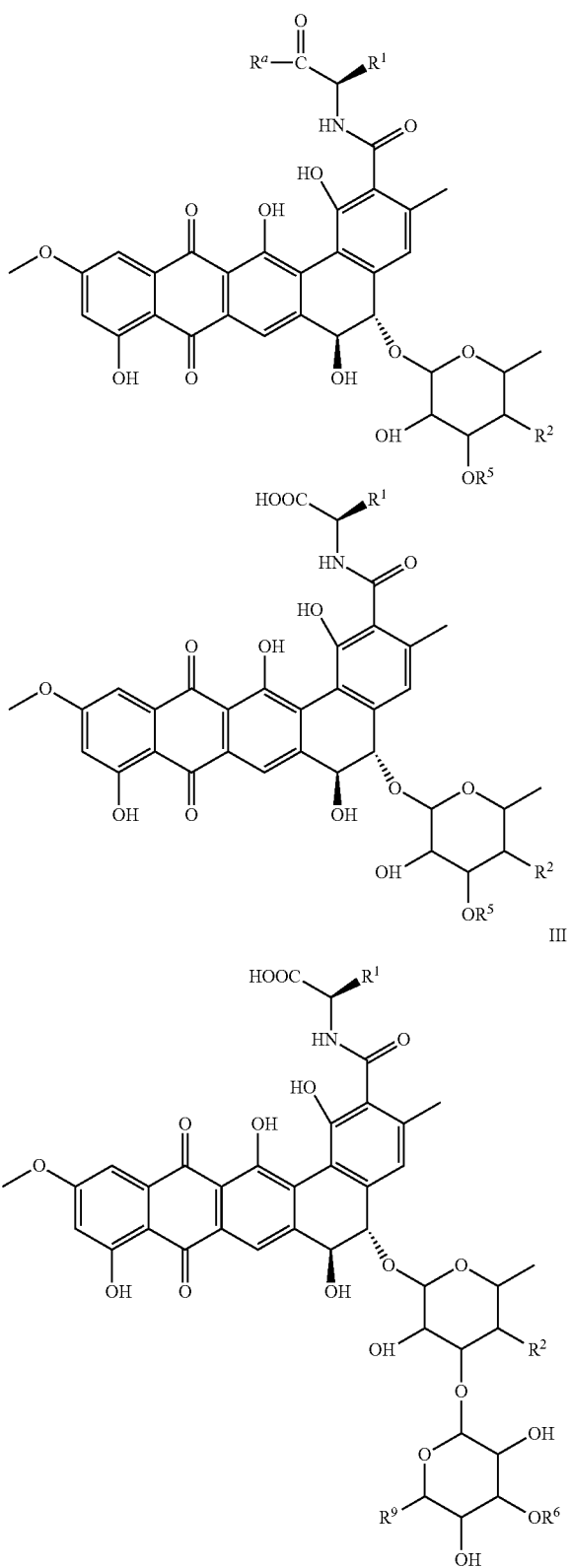

wherein
R$^a$ is selected from the group consisting of OH, —NR$^7$R$^8$, —NHNR$^7$R$^8$, —NHCH$_2$CO$_2$H and (D)-NHCH(CH$_3$)

CO$_2$H; R$^7$ is H and R$^8$ is selected from the group consisting of H, (C$_{1-6}$)alkyl, (C$_{3-6}$)cycloalkyl, (C$_{6-10}$) aryl, and (C$_{7-15}$)aralkyl; or R$^7$ and R$^8$ are independently (C$_{1-6}$)alkyl; or R$^7$, R$^8$ and the nitrogen to which they are attached form a 3- to 6-membered ring R$^1$ is H, methyl, or hydroxymethyl;

R$^2$ is OH or NR$^3$R$^4$, wherein R$^3$ and R$^4$ are independently selected from the group consisting of H; optionally substituted (C$_{1-5}$)alkyl; optionally substituted (C$_{2-5}$) alkenyl; (C$_{2-5}$)alkynyl, wherein the substituent for both the alkyl and alkenyl is a group selected from the group consisting of, carboxy, (C$_{1-5}$)alkoxydarbonyl, carbamyl, (C$_{1-5}$)alkylcarbamyl, di(C$_{1-5}$)alkylcarbamyl, and sulfonyl; (C$_{1-5}$)alkanoyl substituted with a group selected from the group consisting of amino, (C$_{1-5}$) alkylamino, and di(C$_{1-5}$)alkylamino; L-glutamyl; formyl; benzyl; p-tolylsulfonylcarbamyl; —CN; —NO;

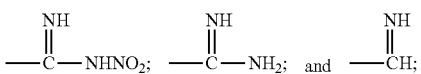

R$^5$ is H or R$^5$ is represented by the general formula II:

II

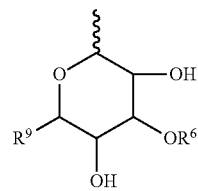

wherein ∿ represents the point of attachment to the oxygen atom of structural formula I or to the oxygen atom of structural formula A;

R$^6$ is H or sulfonic acid;

R$^9$ is H or CH$_2$OH;

and/or a pharmaceutical acceptable addition salt thereof and/or a stereoisomer thereof and/or a solvate thereof;

as a medicine for the prevention or treatment of a kinetoplastid infection in an animal, mammal or human.

The present invention also concerns the use of a compound having formula A, I or III, for use as a medicine for the prevention or treatment of a kinetoplastid infection, including a *Trypanosoma* infection and *Leishmania* infection, in an animal, preferably a mammal, and more preferably a human. The present invention also concerns the use of a compound having formula A, I or III for the manufacture of a medicament for the prevention or treatment of a kinetoplastid infection in an animal, preferably a mammal, and more preferably a human.

In more specific embodiments of the invention, said kinetoplastid infection is an infection with a *Trypanosoma* parasite. In other specific embodiments of the invention, said kinetoplastid infection is an infection with a *Leishmania* parasite. In even more particular embodiments of the invention, said kinetoplastid infection is an infection with *Trypanosoma brucei, Trypanosoma cruzi* or *Leishmania donovani*.

The present invention also concerns a pharmaceutical composition comprising a therapeutically effective amount of a compound having formula A, I, or III and one or more pharmaceutically acceptable excipients for use as a medicine for the prevention or treatment of a kinetoplastid infection in an animal, mammal or human. Said composition may further comprise one or more biologically active drugs being selected from antibiotics and current used medicines for treatment of these parasites, particularly in a safe, non-toxic dose which causes preferentially less or no side effects.

The present invention also concerns a method of prevention or treatment of a kinetoplastid infection, including a *Trypanosoma* infection, in an animal, comprising the administration of a therapeutically effective amount of a compound having formula A, I or III optionally in combination with one or more pharmaceutically acceptable excipients.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Numbered statements of the invention are:
1. The use of a compound having the general formula A or I:

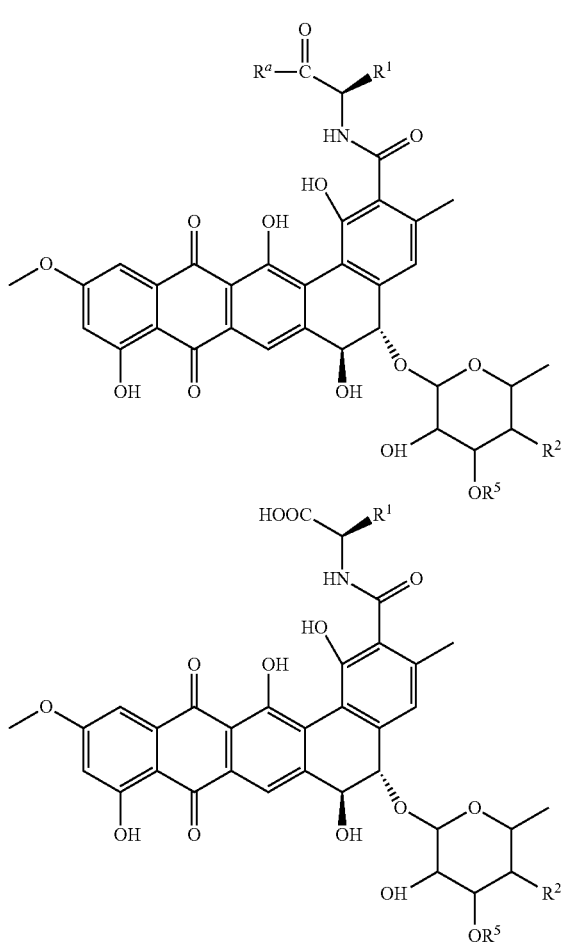

wherein
$R^a$ is selected from the group consisting of OH, —$NR^7R^8$, —$NHNR^7R^8$, —$NHCH_2CO_2H$ and (D)-$NHCH(CH_3)CO_2H$; $R^7$ is H and $R^8$ is selected from the group consisting of H, $(C_{1-6})$alkyl, $(C_{3-6})$cycloalkyl, $(C_{6-10})$aryl, and $(C_{7-15})$aralkyl; or $R^7$ and $R^8$ are independently $(C_{1-6})$alkyl; or $R^7$, $R^8$ and the nitrogen to which they are attached form a 3- to 6-membered ring;

$R^1$ is H, methyl, or hydroxymethyl;
$R^2$ is OH or $NR^3R^4$, wherein $R^3$ and $R^4$ are independently selected from the group consisting of H; optionally substituted $(C_{1-5})$alkyl; optionally substituted $(C_{2-5})$alkenyl; $(C_{2-5})$alkynyl, wherein the substituent for both the alkyl and alkenyl is a group selected from the group consisting of, carboxy, $(C_{1-5})$alkoxycarbonyl, carbamyl, $(C_{1-5})$alkylcarbamyl, di$(C_{1-5})$alkylcarbamyl, and sulfonyl; $(C_{1-5})$alkanoyl substituted with a group selected from the group consisting of amino, $(C_{1-5})$alkylamino, and di$(C_{1-5})$alkylamino; L-glutamyl; formyl; benzyl; p-tolylsulfonylcarbamyl; —CN; —NO;

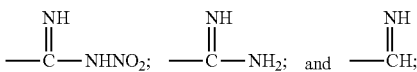

$R^5$ is H or $R^5$ is represented by the general formula II:

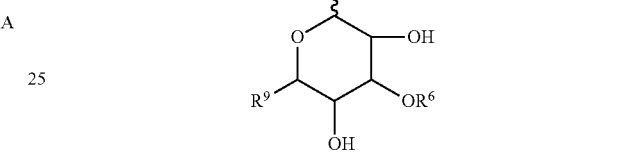

wherein ∿ represents the point of attachment to the oxygen atom of structural formula I or to the oxygen atom of structural formula A;
wherein $R^6$ is H or sulfonic acid; and
wherein $R^9$ is H or $CH_2OH$;
and/or a pharmaceutical acceptable addition salt thereof and/or a stereoisomer thereof and/or a solvate thereof;
as a medicine for the prevention or treatment of a kinetoplastid infection in an animal, mammal or human.

2. The use according to statement 1, wherein the kinetoplastid infection is a trypanosomatid infection or a *Leishmania* infection.
3. The use according to statement 2, wherein the trypanosomatid infection is a *Trypanosoma brucei* infection or a *Trypanosoma cruzi* infection.
4. The use according to statement 2, wherein the *Leishmania* infection is a *Leishmania donovani* infection.
5. The use according to any of statements 1 to 4, wherein
$R^1$ is H, methyl, or hydroxymethyl;
$R^2$ is OH or $NR^3R^4$, wherein $R^3$ and $R^4$ are independently selected from the group consisting of H; $(C_{1-5})$alkyl; $(C_{2-5})$alkenyl; $(C_{2-5})$alkynyl,
$R^5$ is H or $R^5$ is represented by the general formula II:

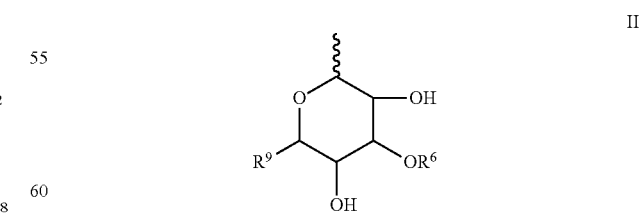

wherein ∿ represents the point of attachment to the oxygen atom of structural formula A or to the oxygen atom of structural formula I;
wherein $R^6$ is H or sulfonic acid; and
wherein $R^9$ is H or $CH_2OH$.

6. The use according to any of statements 1 to 4, wherein $R^3$ is H or methyl and $R^4$ is selected from the group consisting of optionally substituted $(C_{1-5})$alkyl; optionally substituted $(C_2\text{-}5)$alkenyl; $(C_2\text{-}5)$alkynyl, wherein the substituent for both the alkyl and alkenyl is a group selected from the group consisting of carboxy, $(C_{1-5})$alkoxycarbonyl, carbamyl, $(C_{1-5})$alkylcarbamyl, di$(C_{1-5})$alkylcarbamyl, and sulfonyl; $(C_{1-5})$alkanoyl substituted with a group selected from the group consisting of amino, $(C_{1-5})$alkylamino, and di$(C_{1-5})$alkylamino; L-glutamyl; formyl; benzyl; p-tolylsulfonylcarbamy; —CN; —NO;

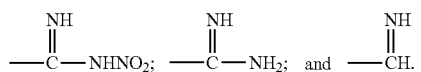

7. The use according to any of statements 1 to 4, wherein $R^3$ is H or $(C_{1-5})$alkyl and $R^4$ is selected from the group consisting of; —CN; —NO;

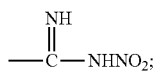

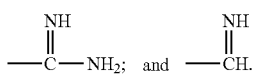

8. The use according to any of statements 1 to 6, wherein when $R^1$ is methyl or hydroxymethyl, the resulting amino acid residue has the D configuration.

9. The use according to any of statements 1 to 4, wherein the compound is selected from the group consisting of: PRM-A; PRM-S, PRM-FA1; BMY28864; or BMS181184.

10. A Method of treating or preventing a kinetoplastid infection in an animal, mammal or human by using the compounds according to formula A or I, pharmaceutically acceptable salts, solvates, tautomers, isomers thereof,

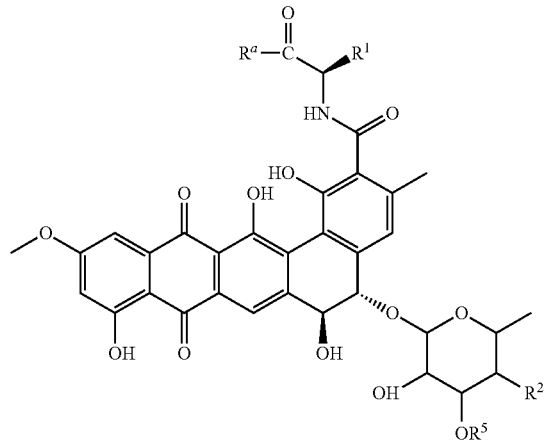

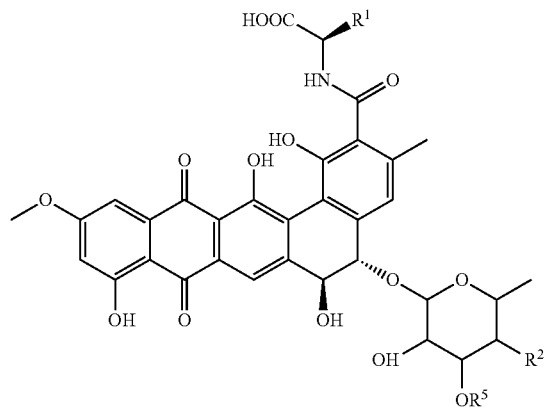

wherein
$R^a$ is selected from the group consisting of OH, —NR$^7$R$^8$, —NHNR$^7$R$^8$, —NHCH$_2$CO$_2$H and (D)-NHCH(CH$_3$CO$_2$H; R$^7$ is H and R$^8$ is selected from the group consisting of H, $(C_{1-6})$alkyl, $(C_{3-6})$cycloalkyl, $(C_{6-10})$aryl, and $(C_{7-15})$aralkyl; or R$^7$ and R$^8$ are independently $(C_{1-6})$alkyl; or R$^7$, R$^8$ and the nitrogen to which they are attached form a 3- to 6-membered ring;

$R_1$ is H, methyl, or hydroxymethyl;
$R^2$ is OH or NR$^3$R$^4$, wherein R$^3$ and R$^4$ are independently selected from the group consisting of H; optionally substituted $(C_{1-5})$alkyl; optionally substituted $(C_{2-5})$alkenyl; $(C_{2-5})$ alkynyl, wherein the substituent for both the alkyl and alkenyl is a group selected from the group consisting of, carboxy, $(C_{1-5})$alkoxycarbonyl, carbamyl, $(C_{1-5})$alkylcarbamyl, di$(C_{1-5})$alkylcarbamyl, and sulfonyl; $(C_{1-5})$alkanoyl substituted with a group selected from the group consisting of amino, $(C_{1-5})$alkylamino, and di$(C_{1-5})$alkylamino; L-glutamyl; formyl; benzyl; p-tolylsulfonylcarbamyl; —CN; —NO;

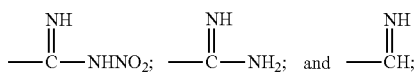

$R^5$ is H or $R^5$ is represented by the general formula II:

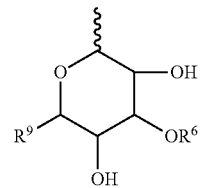

wherein $\sim\!\sim$ represents the point of attachment to the oxygen atom of structural formula I or to the oxygen atom of structural formula A; and
wherein $R^6$ is H or sulfonic acid;
wherein $R^9$ is H or CH$_2$OH.

DETAILED DESCRIPTION OF THE INVENTION

Inventors have found that a series of non-peptidic carbohydrate binding agents (CBAs) are able to specifically interact with surface glycoproteins giving rise to toxic events in bloodstream forms of *Trypanosoma* sp. and the CBAs were also active against *Leishmania*. Hence, nonpeptidic CBAs are a useful tool against African trypanosomiasis, Chagas disease and leishmaniasis.

Pradimicin A (PRM-A) and its analog pradimicin S (PRM-S) are non-peptidic (PRM) mannose-binding agents from prokaryotic origin, which have earlier been investigated for their retroviral, HCV, and SARS-coronavirus inhibiting properties. PRM-A and PRM-S are actinomycetes (*Actinomadura hibisca* and *Actinomadura spinosa* strain A A08 51, respectively)-derived D-mannose-binding agents described as 'lectin-mimic antibiotics'. Activity has been identified against fungi, yeast and several viruses including HIV and HCV (Ueki et al., 1993; Bertaux et al., 2007; Balzarini et al., 2007; Balzarini et al., 2010). This has led to the development of new compounds like BMY28864 and BMS181184 that have similar activity against the pathogens tested but better solubility.

In this invention it is shown that non-peptidic CBAs like PRM-S are effective controlling parasitaemia in an in vivo model system of sleeping sickness, increasing the survival of mice, contrary to what was expected considering previous results with peptidic CBAs on procyclic forms of *Trypanosoma brucei* (Pearson et al., 2000). In addition we show that the CBAs are active against the parasites *Trypanosoma cruzi* and *Leishmania donovani* when cultured in vitro.

Thus, a first aspect of the present invention refers to the use of the following compounds of formula A or I:

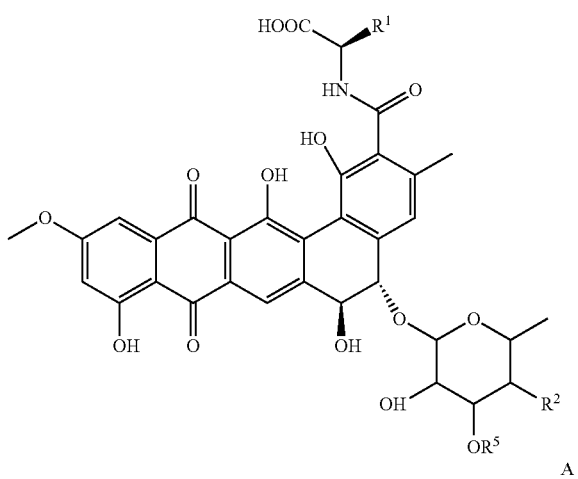

A

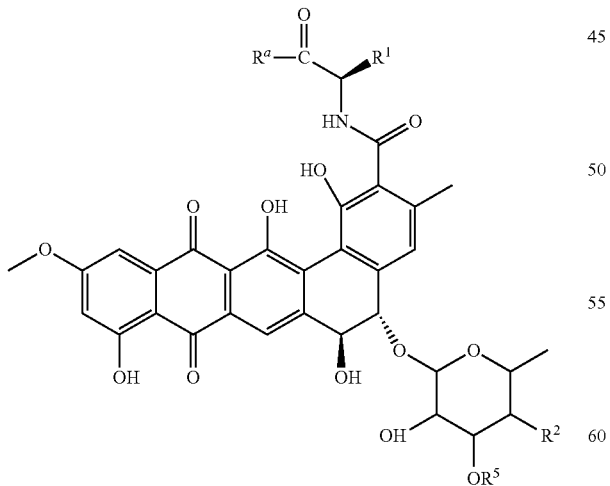

Wherein
$R^a$ is selected from the group consisting of OH, —$NR^7R^8$, —$NHNR^7R^8$, —$NHCH_2CO_2H$ and (D)-NHCH(CH$_3$)CO$_2$H; $R^7$ is H and $R^8$ is selected from the group consisting of H, (C$_{1-6}$)alkyl, (C$_{3-6}$)cycloalkyl, (C$_{6-10}$)aryl, and (C$_{7-15}$)aralkyl; or $R^7$ and $R^8$ are independently (C$_{1-6}$)alkyl; or $R^7$, $R^8$ and the nitrogen to which they are attached form a 3- to 6-membered ring;

$R^1$ is H, methyl, or hydroxymethyl;
$R^2$ is OH or $NR^3R^4$, wherein $R^3$ and $R^4$ are independently selected from the group consisting of H; optionally substituted (C$_{1-5}$)alkyl; optionally substituted (C$_{2-5}$) alkenyl; (C$_{2-5}$) alkynyl, wherein the substituent for both the alkyl and alkenyl is a group selected from the group consisting of, carboxy, (C$_{1-5}$)alkoxycarbonyl, carbamyl, (C$_{1-5}$)alkylcarbamyl, di(C$_{1-5}$)alkylcarbamyl, and sulfonyl; (C$_{1-5}$)alkanoyl substituted with a group selected from the group consisting of amino, (C$_{1-5}$) alkylamino, and di(C$_{1-5}$)alkylamino; L-glutamyl; formyl; benzyl; p-tolylsulfonylcarbamyl; —CN; —NO;

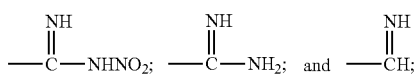

$R^5$ is H or $R^5$ is represented by the general formula II:

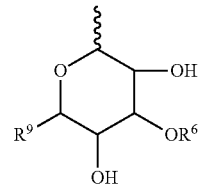

II wherein ⁀ represents the point of attachment to the oxygen atom of structural formula A or to the oxygen atom of structural formula I;
wherein $R^6$ is H or sulfonic acid; and
wherein $R^9$ is H or CH$_2$OH;
and/or a pharmaceutical acceptable addition salt thereof and/or a stereoisomer thereof and/or a solvate thereof;
as a medicine for the prevention or treatment of a kinetoplastid infection in an animal, mammal or human.

A more specific embodiment of the present invention relates to the use of the compounds of structural formula III:

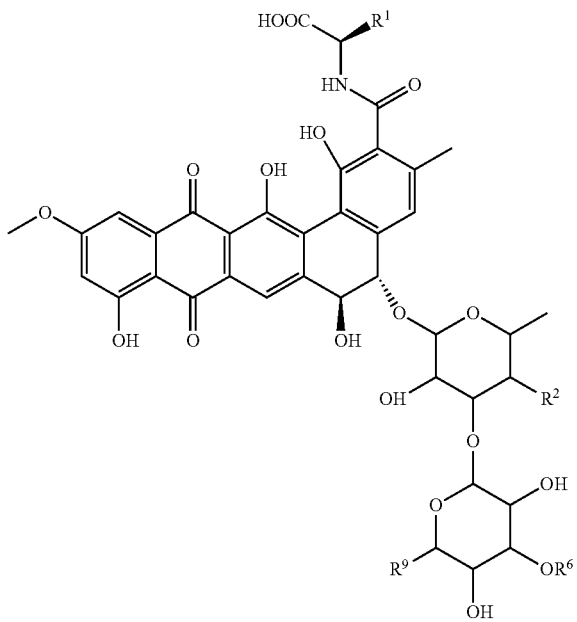

III wherein
R¹ is selected from the group consisting of hydrogen, methyl or hydroxymethyl;
R² is selected from the group consisting of hydroxyl, or NR³R⁴, wherein R³ and R⁴ are independently selected from the group consisting of H, $(C_{1-5})$alkyl, $(C_{2-5})$alkene or $(C_{2-5})$alkynyl.
R⁶ is a hydrogen or a sulfonic acid;
R⁹ is H or $CH_2OH$;
and/or a pharmaceutical acceptable addition salt thereof and/or a stereoisomer thereof and/or a solvate thereof;
as a medicine for the prevention or treatment of a kinetoplastid infection in an animal, mammal or human.

One embodiment of the present invention concerns a compound according to the invention, including a compound of formula A, including the use of said compound according to the invention, wherein R⁹, R⁶, R⁵, R⁴, R³, and R² have any of the values as described herein and $R^a$ is selected from the group consisting of OH, —NR⁷R⁸, —NHNR⁷R⁸, —NHCH₂CO₂H and (D)-NHCH(CH₃)CO₂H; R⁷ is H and R⁸ is selected from the group consisting of H, $(C_{1-6})$alkyl, $(C_{3-6})$cycloalkyl, $(C_{6-10})$aryl, and $(C_{7-15})$aralkyl; or R⁷ and R⁸ are independently $(C_{1-6})$alkyl; or R⁷, R⁸ and the nitrogen to which they are attached form a 3- to 6-membered ring. In a more specific embodiment said $R^a$ is OH.

One embodiment of the present invention concerns a compound according to the invention, including a compound of formula A, I and III, including the use of said compound according to the invention, wherein, $R^a$, R⁹, R⁶, R⁵, R⁴, R³, and R² have any of the values as described herein and R¹ is methyl. In another embodiment, said R¹ is hydrogen; in another specific embodiment R¹ is hydroxymethyl. In another specific, preferred embodiment, when R¹ is methyl or hydroxymethyl, the resulting amino acid has the D-configuration. In another specific, preferred embodiment, when R¹ and/or $R^a$ are chosen such that the resulting amino acid(s) can have two configurations, D and L, the D-configuration is preferred.

In a preferred embodiment of compounds of formula A, including the use of said compounds according to the invention, $R^a$ is selected from the group consisting of amino, $(C_{1-6})$alkylamino, di$(C_{1-6})$alkylamino, hydrazino, glycyl and D-alanyl. Alkyl is more preferably from one to four carbon atoms. In another preferred embodiment of compounds of formula A, including the use of said compounds according to the invention, $R^a$ is selected from the group consisting of amino, $(C_{1-4})$alkylamino, di$(C_{1-4})$alkylamino, hydrazino, —NHCH₂CO₂H and (D)-NHCH(CH₃)CO₂H. In another preferred embodiment of compounds of the present invention, including the compounds of Formula A, including the use of said compounds according to the invention, R¹ is methyl. In yet another preferred embodiment of compounds of the present invention, including the compounds of Formula A, including the use of said compounds according to the invention, R³ is H and R⁴ is H or methyl, or R³ and R⁴ are both methyl; more preferably R³ is H and R⁴ is methyl. In another preferred embodiment of the present invention, including the compounds of Formula A, including the use of said compounds according to the invention, R¹ is methyl, R⁵ is β-D-xylosyl, R³ is H and R⁴ is methyl. In a more specific embodiment $R^a$ is selected from the group consisting of amino, methylamino, dimethylamino, butylamino, hydrazino, —NHCH₂CO₂H and (D)-NHCH(CH₃)CO₂H.

One embodiment of the present invention concerns a compound according to the invention, including a compound of formula A, I and III, including the use of said compound according to the invention, wherein, R² is OH. In another specific embodiment said R² is NR³R⁴, wherein R³ and R⁴ are independently selected from the group consisting of H, $(C_{1-5})$alkyl, $(C_{2-5})$alkene or $(C_{2-5})$alkynyl. In a more specific embodiment said R³ is H or $(C_{1-5})$alkyl. In another specific embodiment said R³ is H or methyl. In a more specific embodiment said R³ is H. In another specific embodiment said R³ is methyl. In a more specific embodiment said R³ is H and R⁴ is methyl. In another specific embodiment, said R³ is H or methyl and said R⁴ is selected from the group consisting of optionally substituted $(C_{1-5})$alkyl; optionally substituted $(C_{2-5})$alkenyl; $(C_{2-5})$alkynyl, wherein the substituent for both the alkyl and alkenyl is a group selected from the group consisting of carboxy, $(C_{1-5})$alkoxycarbonyl, carbamyl, $(C_{1-5})$alkylcarbamyl, di$(C_{1-5})$alkylcarbamyl, and sulfonyl; $(C_{1-5})$alkanoyl substituted with a group selected from the group consisting of amino, $(C_{1-5})$alkylamino, and di$(C_{1-5})$alkylamino; L-glutamyl; formyl; benzyl; p-tolylsulfonylcarbamyl. In another specific embodiment said R³ is H or $(C_{1-5})$alkyl and said R⁴ is —CN; —NO;

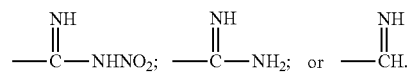

In another more specific embodiment R³ is H or methyl and said R⁴ is —CN; —NO;

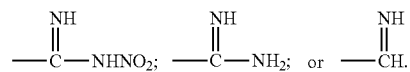

Another specific embodiment of the present invention concerns a compound according to the invention, including a compound of formula A, I and III, including the use of said compound according to the invention, wherein R² is NHN, N(CH₃)CN, N(CH₃)NO,

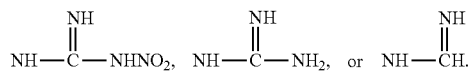

In a more specific embodiment the present invention concerns a compound according to the invention, including a compound of formula A, I and III, including the use of said compound according to the invention, wherein R¹ is hydrogen, methyl or hydroxymethyl, provided that when R¹ is methyl or hydroxymethyl, the resulting amino acid has the D configuration and wherein R² is NHCN, N(CH₃)CN, N(CH₃)NO,

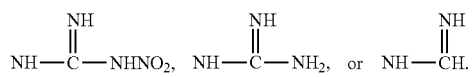

In yet a more specific embodiment thereof, R⁶ is H and R⁹ is H in formula III and in formula A and I, R⁵ is represented by the general formula II,

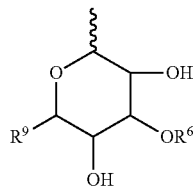

II wherein ⌇ represents the point of attachment to the oxygen atom of structural formula A or to the oxygen atom of structural formula I;
wherein $R^6$ is H and $R^9$ is H.

In another specific embodiment $R^5$ is represented by the general formula II,

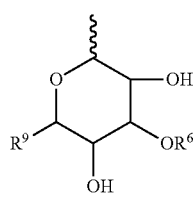

II wherein ⌇ represents the point of attachment to the oxygen atom of structural formula A or to the oxygen atom of structural formula I;
wherein $R^6$ is H or sulfonic acid; and
wherein $R^9$ is H or $CH_2OH$.

In a more specific embodiment, said $R^6$ is H; in another specific embodiment said $R^6$ is sulfonic acid; in another specific embodiment said $R^9$ is H. In another specific embodiment said $R^6$ is H and said $R^9$ is H.

Another embodiment of the present invention concerns a compound according to the invention, including a compound of formula A and I, including the use of said compound according to the invention, wherein, $R^a$, $R^4$, $R^3$, $R^2$ and $R^1$ have any of the values as described herein and $R^5$ is H.

Another embodiment of the present invention concerns a compound according to the invention, including a compound of formula A, I and III, including the use of said compound according to the invention, wherein, $R^a$, $R^6$, $R^5$, and $R^1$ have any of the values as described herein and $R^2$ is $NR^3R^4$, wherein $R^3$ is H or $(C_{1-5})$alkyl, such as methyl, and $R^4$ is H or $(C_{1-5})$alkyl, such as methyl. In another more specific embodiment said $R^3$ is H and said $R^4$ is methyl. In another specific embodiment $R^3$ and $R^4$ are both methyl.

Another embodiment of the present invention concerns a compound according to the invention, including a compound of formula A, I and III, including the use of said compound according to the invention, wherein $R^a$, $R^6$, $R^5$, $R^2$ and $R^1$ have any of the values as described herein and wherein, $R^9$ is H or $CH_2OH$; in a more specific embodiment $R^9$ is H.

Another embodiment of the present invention concerns a compound according to the invention, including a compound of formula A, I and III, including the use of said compound according to the invention, wherein $R^a$, $R^g$, $R^6$, $R^5$, and $R^1$ have any of the values as described herein and $R^2$ is OH.

The sugar amino group of the compounds of the present invention, including all pradimicins and derivatives thereof are optionally protected. The protecting groups for the amino group are not particularly limited but may be any that can be put on and removed easily without adversely affecting the rest of the molecules. Suitable amino protecting groups include benzyloxycarbonyl, t-butoxycarbonyl, toluenesulfonyl, trifluoroacetyl and chloroacetyl. The selection of amino and/or carboxyl protecting groups, and methods of blocking and deblocking the non-reacting amino and/or carboxyl groups are discussed in monographs such as "Protective Groups in Organic Chemistry" J. F. W. McOmie Plenum Press, 1973 and "Peptide Synthesis" M. Bodansky et al, Wiley, 1976, and are generally within the skills of one of ordinary skill in organic synthesis.

A detailed description of certain compounds of the present invention, including pradimicin and analogues, intermediates and derivatives thereof, their synthesis and their antifungal use are described in EP388982, EP428132, EP432527, EP580480 and EP584014.

A second aspect of the invention are pharmaceutical compositions for treating infections by kinetoplastid parasites such as trypanosomatid parasites comprising an effective amount of the agent of formula A, I or III and a pharmaceutically acceptable carrier.

A third aspect of the invention relates to a method of prevention or treatment of a kinetoplastid parasite infection, including a trypanosomatid parasite infection, in an animal, a mammal or human, comprising the administration of a therapeutically effective amount of a compound having formula A, I, or III, optionally in combination with one or more pharmaceutically acceptable excipients.

Definitions

As used herein, unless indicated otherwise, "alkyl" includes straight and branched carbon chains. As used herein with respect to a substituting radical, and unless otherwise stated, the term "$(C_{1-6})$alkyl" means straight and branched chain saturated acyclic hydrocarbon monovalent radicals having from 1 to 6 carbon atoms such as, for example, methyl, ethyl, propyl, n-butyl, 1-methylethyl (isopropyl), 2-methylpropyl (isobutyl), 1,1-dimethylethyl (ter-butyl), 2-methylbutyl, n-pentyl, dimethylpropyl, n-hexyl, 2-methylpentytl, 3-methylpentyl and the like. By analogy, the term "$(C_{1-5})$alkyl" refers to such radicals having from 1 to 5 carbon atoms, i.e. up to and including pentyl; and the term "$(C_{1-4})$alkyl" refers to such radicals having from 1 to 4 carbon atoms.

"Pharmaceutically acceptable salt" and "Pharmaceutically acceptable addition salt" may be an internal salt; an organic or inorganic base salt, such as the sodium, potassium, lithium, ammonium, and trialkylammonium salt; or an acid addition salt with a mineral acid or an organic acid, e.g. the hydrochloride, sulfate, hydrogen sulfate, phosphate, formate, fumarate, succinate and acetate salt.

As used herein with respect to a substituting radical, and unless otherwise stated, the term "$(C_{3-6})$cycloalkyl" means a cyclic saturated hydrocarbon monovalent radical having from 3 to 6 carbon atoms, such as for instance cyclopropyl, cyclobutyl, cyclopentyl, cyclohexyl, and the like.

An amino substituted $(C_{1-5})$alkanoyl includes the carbamyl radical; similarly, a mono- or dialkylamino-substituted $(C_{1-5})$alkanoyl includes the correspondingly substituted carbamyl radical.

"Pradimicin" refers to a member of the naturally occurring pradimicins, benanomicins, their desxylosyl derivatives, and their respective salts.

third dose of 25 mg·kg$^{-1}$, even after reaching a high parasite concentration. However, parasitaemia was resumed in mice treated with 25 mg·kg$^{-1}$, exhibiting a mean relapse day (MRD) of 10.7±0.6. The MSD for 25 mg·kg$^{-1}$ and 50 mg·kg$^{-1}$ dosages were extended to 18.0±7 or >90, respectively (Table 2 and FIG. 2A).

Figure 2:
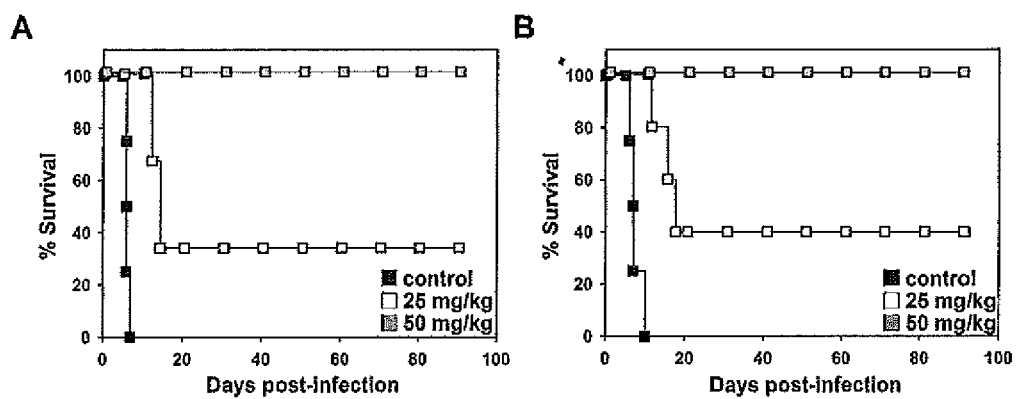
FIG. 2. Survival analysis of mice infected with trypanosomes and treated with PRM-S. One dose per day of 25 mg·kg$^{-1}$ or 50 mg·kg$^{-1}$ of PRM-S was administered to mice for four consecutive days from day three post-infection. A) Kaplan-Meier survival analysis of C57BL/6J mice infected with *T. brucei brucei* 427 (single-marker) cell line and treated with PRM-S or with the vehicle as control. B) Kaplan-Meier survival analysis of BALB/c mice infected with *T. brucei rhodesiense* EATRO3 strain and treated with PRM-S or with the vehicle as control.

On the other hand, untreated BALB/c-mice infected with *T. b. rhodesiense* died between the 6th and the 10th day post-infection resulting in a MSD of 7.5±1.7, while the MSD for animals treated with 25 mg·kg$^{-1}$ and 50 mg·kg$^{-1}$ of PRM-S were extended to 44.4±41.7 and >90, respectively (Table 2 and FIG. 2B). With both dosages, the parasitaemia was drastically reduced after the first administration of PRM-S, to appear subsequently in the case of 25 mg·kg$^{-1}$ in three of the five mice tested and exhibiting a MRD of 10.7±0.6 (Table 2).

TABLE 2

In vivo activities of PRM-S against *T. brucei*

| Parasites | Mice | CBA | dose mg·kg$^{-1}$ | route | cured/ infected | MSD | MRD |
|---|---|---|---|---|---|---|---|
| *T. b. rhodesiense* EATRO3 | BALB/c | vehicle | | i.p. | 0/4 | 7.5 ± 1.7 | |
| | | PRMS | 4 × 25 | i.p. | 2/5 | 44.4 ± 41.7 | 10.7 ± 0.6 |
| | | | 4 × 50 | i.p. | 5/5 | >90 | |
| *T. b. brucei* 427 | C57BL/6J | vehicle | | i.p. | 0/4 | 6.25 ± 0.5 | |
| | | PRMS | 4 × 25 | i.p. | 0/3 | 18.0 ± 7 | 10.7 ± 0.6 |
| | | | 4 × 50 | i.p. | 6/6 | >90 | |

EXAMPLES

Example 1. Activity In Vitro of PRM-S, PRM-A, PRM-FS and FA1-Mono Sugar Against *T. brucei*

Figure 1:
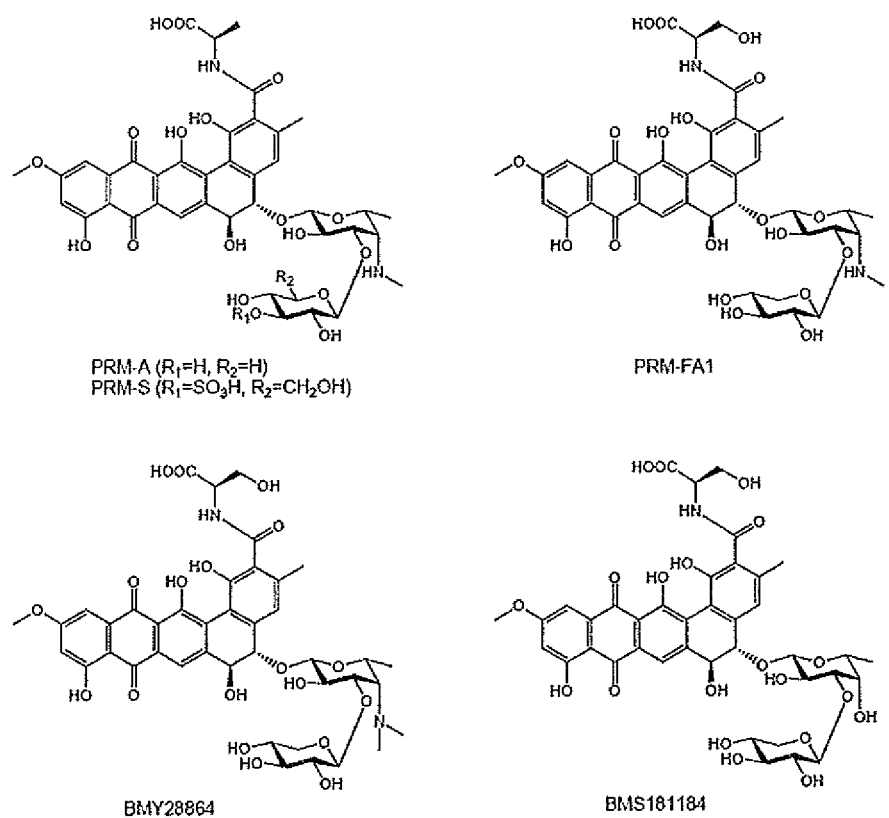
FIG. 1. Structures of Pradimicin-FS, Pradimicin-S, Pradimicin-A, BMY288864 and BMS181184.

The non-peptidic CBAs, PRM-A and PRM-S (FIG. 1) are active in vitro in the low micromolar range against *Trypanosoma brucei brucei* as can be seen in Table 1.

TABLE 1

EC$_{50}$ values for prokaryote-derived CBAs against *T. brucei* BSF.

| CBA | Specificity | EC$_{50}$ (µg · mL$^{-1}$) | EC$_{50}$ (µM) |
|---|---|---|---|
| PRM-S | α(1,2) Man | 5.85 ± 0.08 | 6.44 ± 0.08 |
| PRM-A | α (1,2) Man | 3.20 ± 0.04 | 3.80 ± 0.05 |
| PRM-FS | α (1,2) Man | 13.0 ± 0.7 | 13.5 ± 0.8 |
| FA1-mono sugar | α (1,2) Man | 24.3 ± 2.1 | 33.3 ± 2.8 |

Example 2. Activity In Vivo of PRM-S Against *T. brucei*

In order to establish the trypanocidal capacity of PRM-S, C57BL/6J or BALB/c mice were infected with *T. b. brucei* 427 or *T. b. rhodesiense* EATRO3 strains, respectively, and infection was allowed to proceed for 3 days before treatment with PRM-S, one dosage per day for 4 days.

In the case of C57BL/6J mice infected with *T. b. brucei*, untreated mice died between the 6th and 7th day post-infection when parasitaemia reached around 1×10$^9$ cells*mL$^{-1}$, thus a mean survival day (MSD) of 6.25±0.5 was obtained (FIG. 2A). In contrast, PRM-S administration starting at the 3rd day post-infection, when parasitaemia reached 1×10$^7$ cells·mL$^{-1}$, resulted in a dramatic decrease of parasitaemia after the first dose of 50 mg·kg$^{-1}$, or after the Example 3. Activity In Vitro of P-RM-S and PRM-A Against *L. donovani* and *T. cruzi*

As can be seen in Tables 3 and 4, the non-peptidic carbohydrate binding agents PRM-S and PRM-A are active against different stages of *T. cruzi* and *L. donovani* parasites cultured in vitro. Pradimicin-S and pradimicin-A were active at low micromolar concentrations against amastigotes of *Leishmania donovani*, the intracellular stage of the parasite present in the human host and they were also active against *L. donovani* promastigotes. No toxicity was observed in macrophages (EC$_{50}$>100 µM). In addition, both derivatives induce lysis at low micromolar concentrations of trypomastigote forms of *Trypanosoma cruzi*, the infective stage responsible for invasion of mammalian host cells (Table 4).

TABLE 3

PRM-S and PRM-A activity against *L. donovani*.

| Cell line | CBA | specificity | EC$_{50}$ (µg · mL$^{-1}$) | EC$_{50}$ (µM) |
|---|---|---|---|---|
| *L. donovani* promastigotes | PRM-A | α(1,2) Man | 18.0 ± 0.7 | 21.4 ± 0.8 |
| | PRM-S | α(1,2) Man | 21.8 ± 1.9 | 22.9 ± 1.9 |
| | PRM-Fs | α(1,2) Man | 49.1 ± 2.0 | 50.8 ± 2.1 |
| *L. donovani* amastigotes | PRM-A | α(1,2) Man | 0.7 ± 0.1 | 0.8 ± 0.1 |
| | PRM-S | α(1,2) Man | 2.2 ± 0.2 | 2.3 ± 0.3 |
| Macrophages | PRM-A | α(1,2) Man | >100 | >100 |
| | PRM-S | α(1,2) Man | >100 | >100 |

TABLE 4

PRM-S and PRM-A activity against *T. cruzi*.

| Cell line | CBA | specificity | $EC_{50}$ ($\mu g \cdot mL^{-1}$) | $EC_{50}$ ($\mu M$) |
|---|---|---|---|---|
| *T. cruzi* epimastigotes | PRM-A | α(1,2) Man | 23.6 ± 1.1 | 28.1 ± 1.3 |
|  | PRM-S | α(1,2) Man | 17.3 ± 2.4 | 19.0 ± 2.6 |

| Cell line | drug | specificity | $EC_{50}$ (% Lysis) *T. cruzi* ($\mu g \cdot mL^{-1}$) | $EC_{50}$ (% Lysis) *T. cruzi* ($\mu M$) |
|---|---|---|---|---|
| *T. cruzi* trypomastigotes | PRM-A | α(1,2) Man | 1.0 ± 0.3 | 1.2 ± 0.3 |
|  | PRM-S | α(1,2) Man | 1.2 ± 0.3 | 1.4 ± 0.3 |
|  | Benznidazole |  | 1.35 ± 0.05 | 5.2 ± 0.2 |

Example 4. Material and Methods

Parasite Culture

*Trypanosoma brucei brucei* single-marker bloodstream forms (BSF) (antigenic type 1.2, MITat 1.2, clone 221a) strain 427, harbouring T7 RNA polymerase and the tetracycline repressor (Wirtz et al., 1999) and *Trypanosoma brucei rhodesiense* EATRO3 ETat1.2 TREU164 (Turner et al., 2004) were used in this study. Bloodstream forms were cultured at 37° C. and 5% $CO_2$ in HMI-9 supplemented with 10% (v/v) or 20% fetal bovine serum, respectively. The non-peptidic CBAs pradimicin A (PRM-A, derived from *Actinomadura hibisca*) (Oki et al., 1988) and pradimicin S (PRM-S, derived from *Actinomadura spinosa* strain A A08 51) (Saitoh et al., 1993) were tested for inhibition of parasite growth.

In Vivo Studies

Female C57BL/6 or BALB/c mice (Jackson Laboratories, Bar Harbor, Me.) were split in groups containing between three and six mice (6-8 weeks old), and infected via intraperitoneal route with $5 \times 10^3$ (*T. b. brucei* strain 427) or $1 \times 10^4$ (*T. b. rhodesiense* EATRO3) trypanosomes, respectively. Different dosages of PRM-S (25 mg·kg$^1$ and 50 mg·kg$^{-1}$) were administered once/day intraperitoneally (200 μL) for 4 days starting on the third day post-infection, in 0.5% w/v hydroxypropylmethylcellulose (HPMC), 0.4% v/v Tween 80 and 0.5% v/v benzyl alcohol used as dosage formulation. One group of mice in each case was also infected and treated with the vehicle as control, Parasitaemia was monitored daily in a haematocytometer under a microscope from the third day post-infection and after tail blood extraction.

Activity In Vitro Against *L. donovani*

Activity of pradimicin A (PRM-A) and S (PRM-S) was tested against promastigote and amastigote forms of *L. donovani* MHOM/ET/67HU3.

In the case of the promastigote forms, $2.5 \times 10^4$ parasites were incubated in 24-well plates (1 mL) for 48 h at different drug concentrations between 0.391 μg·mL$^{-1}$ and 50 μg·mL$^{-1}$ in RPMI 1640 modified supplemented with 20% FBS, 2 mM L-glutamine, 100 U·mL$^{-1}$ penicillin and 100 μg·mL$^{-1}$ of streptomycin. The proliferation was determined by counting the number of cells using a Z1 Coulter counter. $EC_{50}$ values were calculated by nonlinear regression analysis.

To determine activity against the amastigote form, $1 \times 10^5$ mouse peritoneal macrophages were seeded in 24-well tissue culture chamber slides using RPMI 1640 medium supplemented with 10% HIFBS, 2 mM L-glutamine, 100 U·mL-1 penicillin and 100 μg·mL$^{-1}$ streptomycin. Compounds were added and cells were then infected with late-stage promastigotes at a macrophage/parasite ratio of 1:10. After 8 h of infection at 35° C. and 5% $CO_2$, extracellular parasites were removed by washing with serum-free medium, and infected macrophage cultures were incubated with different CBA concentrations for 72 h in RPMI 1640 medium plus 10% HIFBS at 37° C. with 5% $CO_2$. After that, macrophages were fixed with 2.5% p-formaldehyde in PBS for 30 min at 4° C., permeabilized with 0.1% Triton X-100 in PBS for 30 min, and incubated with Gold antifade reagent plus DAPI in order to detect the intracellular parasites. Drug activity was determined from the percentage of infected cells and from the number of amastigotes per cell in drug-treated versus non-treated cultures.

Activity In Vitro Against *T. cruzi*

Activity of pradimicin A (PRM-A) and S (PRM-S) against *T. cruzi* was studied in epimastigote and trypomastigote forms of *T. cruzi* Tulahuen strain C4.

In the case of epimastigote forms, $2 \times 10^5$ parasites were seeded in a 96-wells plate (100 μL) and incubated 3 days with different drug concentrations between 0.0625 μg·mL$^{-1}$ and 100 μg·mL$^{-1}$ in liver infusion tryptose (LIT) medium supplemented with 10% fetal calf serum at 28° C. In the case of trypomastigotes, $1 \times 10^5$ parasites were seeded in a 96-well plate (100 μL) and incubated with different drug concentrations between 0.006 μg·mL$^{-1}$ and 12.5 μg·mL$^{-1}$ for 24 h in RPMI 1640 medium supplemented with 10% FBS, 2 mM L-glutamine, 100 U·mL$^{-1}$ penicillin and 100 μg·mL$^{-1}$ streptomycin at 37° C. and 5% $CO_2$. Cell viability of epimastigotes and lysis percentage of trypomastigotes were determined by adding 10 μL of resazurin (0.11 mg·mL$^{-1}$ in PBS) and measuring fluorescence at 570/590 nm of excitation/emission wavelength after 2 h of incubation using a Spectramax Gemini EM microplate fluorometer (Molecular Devices Cooperation, Sunnyvale, Calif., USA). $EC_{50}$ or 50% lysis values were defined as the drug concentration required for half-maximal inhibition of the cellular growth rate or half-maximal lysis and were calculated by nonlinear regression analysis.

BIBLIOGRAPHY

Balzarini, J., (2007) Targeting the glycans of glycoproteins: a novel paradigm for antiviral therapy. Nat Rev Microbiol 5: 583-597.

Balzarini, J., Francois, K. O., Van Laethem, K., Hoorelbeke, B., Renders, M., Auwerx, J., Liekens, S., Oki, T., Igarashi, Y., and Schols, D. (2010) Pradimicin S, a highly soluble nonpeptidic small-size carbohydrate-binding antibiotic, is an anti-HIV drug lead for both microbicidal and systemic use. Antimicrob Agents Chemother 54: 1425-1435.

Balzarini, J., Van Laethem, K., Daelemans, D., Hatse, S., Bugatti, A., Rusnati, M., Igarashi, Y., Oki, T., and Schols, D. (2007) Pradimicin A, a carbohydrate-binding nonpeptidic lead compound for treatment of infections with viruses with highly glycosylated envelopes, such as human immunodeficiency virus. J Virol 81: 362-373.

Bertaux, C., Daelemans, D., Meertens, L., Cormier, E. G., Reinus, J. F., Peumans, W. J., Van Damme, E. J., Igarashi, Y., Oki, T., Schols, D., Dragic, T., and Balzarini, J. (2007) Entry of hepatitis C virus and human immunodeficiency virus is selectively inhibited by carbohydrate-binding agents but not by polyanions. Virology 366: 40-50.

Morrison, L J., Marcello, L., and McCulloch, R. (2009) Antigenic variation in the African trypanosome: molecular mechanisms and phenotypic complexity. Cell Microbiol 11: 1724-1734.

Oki, T., Konishi, M., Tomatsu, K., Tomita, K., Saitoh, K., Tsunakawa, M., Nishio, M., Miyaki, T., and Kawaguchi, H. (1988) Pradimicin, a novel class of potent antifungal antibiotics. J Antibiot (Tokyo) 41: 1701-1704.

Pearson, T. W., Beecroft, R. P., Welburn, S. C., Ruepp, S., Roditi, I., Hwa, K. Y., Englund, P. T., Wells, C. W., and Murphy, N. B. (2000) The major cell surface glycoprotein procyciin is a receptor for induction of a novel form of cell death in African trypanosomes in vitro. Mol Biochem Parasitol 111: 333-349.

Saitoh, K., Tsuno, T., Kakushima, M., Hatori, M., Furumai, T., and Oki, T. (1993) Pradimicin S, a new pradimicin analg. If. Isolation and structure elucidation. J Antibiot (Tokyo) 46: 406-411.

Turner, C. M., McLellan, S., Lindergard, L. A., Bisoni, L., Tait, A., and MacLeod, A. (2004) Human infectivity trait in *Trypanosoma brucei*: stability, heritability and relationship to sra expression. Parasitology 129: 445-454.

Ueki, T., Numata, K., Sawada, Y., Nishio, M., Ohkuma, H., Toda, S., Kamachi, H., Fukagawa, Y., and Oki, T. (1993) Studies on the mode of antifungal action of pradimicin antibiotics. II. D-mannopyranoside-binding site and calcium-binding site. J Antibiot (Tokyo) 46: 455-464.

Wirtz, E., Leal, S., Ochatt, C., and Cross, G. A. (1999) A tightly regulated inducible expression system for conditional gene knock-outs and dominant-negative genetics in *Trypanosoma brucei*. Mol Biochem Parasitol 99: 89-101.

The invention claimed is:

1. A method of treating a kinetoplastid infection in a subject comprising administering to the subject a compound according to formula A or I in an amount effective to treat a kinetoplastid infection in a subject;

wherein formula A has the structure:

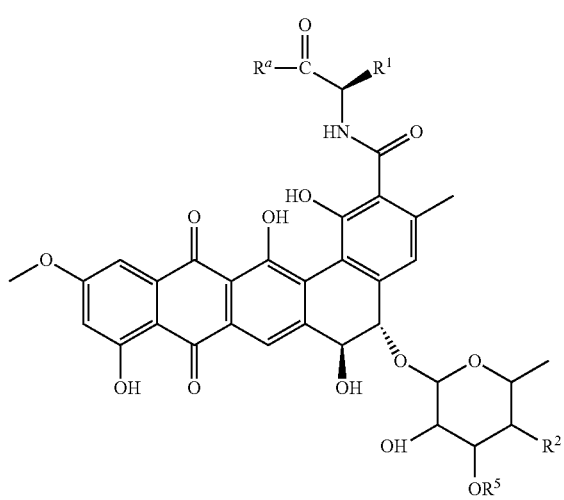

A wherein formula I has the structure:

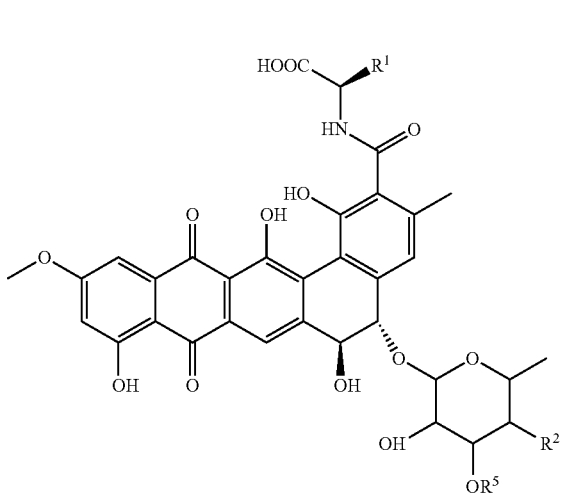

I wherein $R^a$ is OH;

$R^1$ is H, methyl, or hydroxymethyl;

$R^2$ is OH or $NR^3R^4$, wherein $R^3$ and $R^4$ are independently selected from the group consisting of H and $(C_{1-5})$alkyl;

$R^5$ is represented by the general formula II:

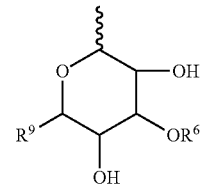

II wherein ～ represents the point of attachment to the oxygen atom of structural formula I or to the oxygen atom of formula A;

wherein $R^6$ is H or sulfonic acid; and wherein $R^9$ is H or $CH_2OH$;

or a pharmaceutically acceptable salt, solvate, tautomer or isomer thereof;

wherein the kinetoplastid infection is a trypanosomatid infection or a *Leishmania* infection:

wherein the *Leishmania* infection is a *Leishmania donovani* infection.

2. The method according to claim 1, wherein the trypanosomatid infection is a *Trypanosoma brucei* infection or a *Trypanosoma cruzi* infection.

3. The method according to claim 1, wherein $R^3$ is H or methyl and $R^4$ is $(C_{1-5})$alkyl.

4. The method according to claim 1, wherein when $R^1$ is methyl or hydroxymethyl, the resulting amino acid residue has the D configuration.

5. The method according to claim 1, wherein the compound is selected from the group consisting of PRM-A; PRM-S, PRM-FA1; BMY28864; and BMS181184

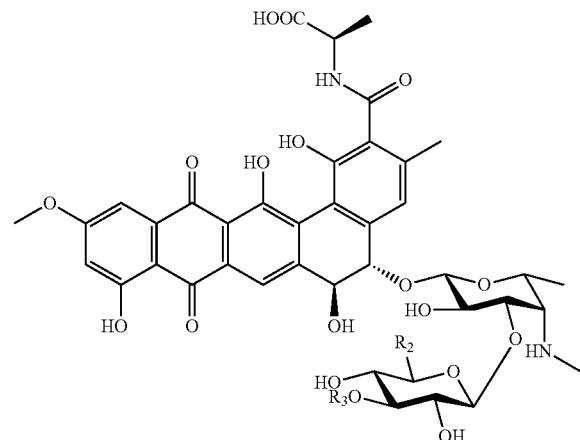

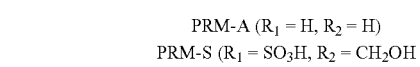

PRM-A ($R_1$ = H, $R_2$ = H)
PRM-S ($R_1$ = $SO_3H$, $R_2$ = $CH_2OH$)

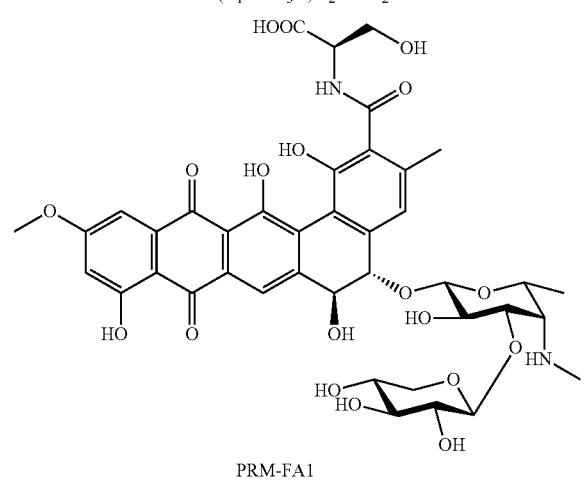

PRM-FA1

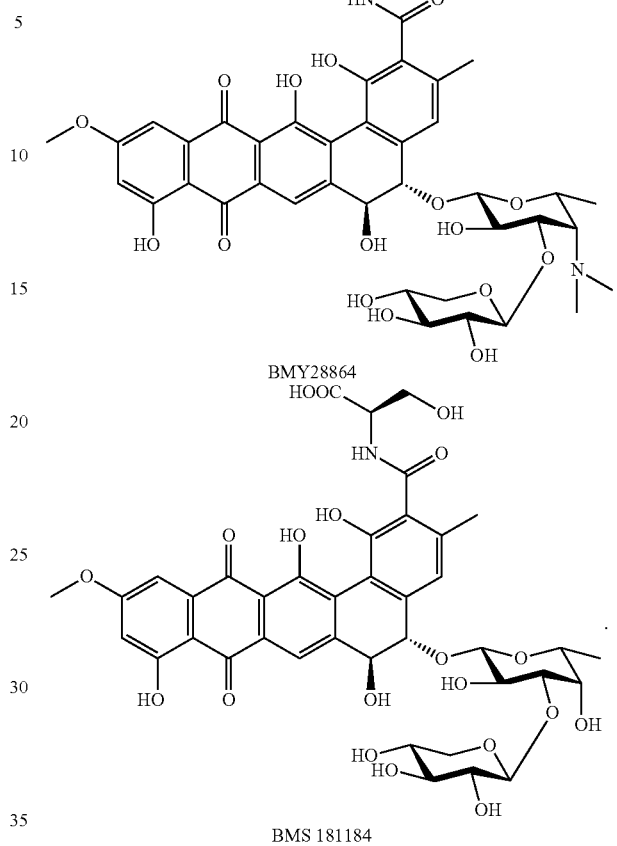

BMY28864

BMS 181184

6. The method according to claim 1, wherein the subject is an animal.

7. The method according to claim 1, wherein the subject is a mammal.

8. The method according to claim 1, wherein the subject is a human.

\* \* \* \* \*